US006592893B1

(12) United States Patent
Gessa

(10) Patent No.: US 6,592,893 B1
(45) Date of Patent: Jul. 15, 2003

(54) TRANSDERMAL PATCH AND TOPICAL COMPOSITIONS COMPRISING PROPYLNORAPOMORPHINE

(75) Inventor: Gian Luigi Gessa, Cagliari (IT)

(73) Assignee: Unihart Corporation, Dublin (IE)

( * ) Notice: Subject to any disclaimer, the term of this patent is extended or adjusted under 35 U.S.C. 154(b) by 0 days.

(21) Appl. No.: 09/743,576

(22) PCT Filed: Jul. 15, 1999

(86) PCT No.: PCT/IE99/00066

§ 371 (c)(1),
(2), (4) Date: Jan. 12, 2001

(87) PCT Pub. No.: WO00/03698

PCT Pub. Date: Jan. 27, 2000

(30) Foreign Application Priority Data

Jul. 17, 1998 (IT) .................................... RM98A0479

(51) Int. Cl.[7] .................... A61F 13/00; A61F 13/02; A61K 9/14

(52) U.S. Cl. .................... 424/449; 424/484; 424/487; 424/448

(58) Field of Search ................... 424/449, 448, 424/443

(56) References Cited

U.S. PATENT DOCUMENTS 4,126,616 A * 11/1978 Hinshaw et al.
5,656,286 A * 8/1997 Miranda et al. ............ 424/448
5,922,341 A * 7/1999 Smith et al. ................. 424/430
5,994,392 A * 11/1999 Shashoua ................... 514/432

FOREIGN PATENT DOCUMENTS

FR     2 732 896 A   * 10/1996

OTHER PUBLICATIONS

Christopher L. Gummer, "The In Vitro Evaluation of Transdermal Delivery," in Hadgraft et al., Transdermal Drug Delivery: Developmental Issues and Research Initiatives (New York: Marcel Dekker, Inc., 1989): 177–196.

Kakuji Tojo, "Design and Calibration of In Vitro Permeation Apparatus," in Chien, Transdermal Controlled Systemic Medications (New York: Marcel Dekker, Inc., 1987): 127–158.

E. Nicolle et al., "Pharmacokinetics of Apomorphine in Parkinsonian Patients," Fundam. Clin. Pharmacol. (1993) 7, 245–252.

E. Sam et al., "Stability of Apomorphine in Plasma and Its Determination by High–Performance Liquid Chromatography with Electrochemical Detection," Journal of Chromatography B, 658 (1994), 311–317.

Donatas Satas, "Coating Equipment," in Satas ed., Handbook of Pressure Sensitive Adhesive Technology (New York: Van Nostrand Reinhold, 1989): 767–808.

(List continued on next page.)

Primary Examiner—Gollamudi S. Kishore
Assistant Examiner—Isis Ghali
(74) Attorney, Agent, or Firm—Griffin & Szipl, P.C.

(57) ABSTRACT

A pharmaceutical composition is characterized by: an active principle selected from one or more components of the group consisting of R(-)-propylnorapomorphine hydrochloride, S(+)-propylnorapomorphine hydrochloride, derivatives of R(-)-propylnorapomorphine hydrochloride and derivatives of S(+)-propylnorapomorphine hydrochloride, in pharmaceutically acceptable and effective doses, and further comprising components selected from the group consisting of stabilizers, solubilizers and permeation activators to facilitate the passage of the active principle through the skin. A transdermal patch that includes the pharmaceutical composition is also disclosed as well as a method of treatment for Parkinson's disease, hemicrania, sexual impotence, and psychotic disorders using the pharmaceutical composition or a transdermal patch that includes the pharmaceutical composition are described.

15 Claims, 4 Drawing Sheets

OTHER PUBLICATIONS

Orland W. Grant et al., "Other Knife and Roll Coaters," in Satas ed., Web Processing and Converting Technology and Equipment (New York: Van Nostrand Reinhold, 1984): 60–80.

Joel J. Elias, "The Microscopic Structure of the Epidermis and Its Derivatives," in Bronaught et al., Percutaneous Absorption (New York: Marcel Dekker, Inc., 1989): 3–12.

John L. Neumeyer et al., "Aporphines. 48. Enantioselectivity of (R)–(–)–and (S)–(+)–N–n–Propylnorapomorphine on Dopamine Receptors," J. Med. Chem. 1983, 26, 516–521.

Advances In Neurology, vol. 60 (1993), "Continuous Subcutaneous Apomorphine Infusions for Fluctuating Parkinson's Disease —Long–Term Follow–up in 18 Patients", W. Poewe et al., pp. 656–659.

Life Sciences, vol. 37 (1985), "Effects of Isomers of Apomorphines on Dopamine Receptors in Striatal and Limbic Tissue of Rat Brain", N. S. Kula et al.; Jul. 15, 1985, pp. 1051–1057.

Journal of Neurology, Neurosurgery and Psychiatry (1992), 55, "Rectal apomorphine: a new treatment modality in Parkinson's disease", T. Van Laar et al., pp. 737–738.

The Journal of Pharmacology And Experimental Therapeutics, vol. 247, No. 1 (1988) , Effects of N–n–Propylnorapomorphine Enantiomers on Single Unit Activity of Substantia Nigra . . . , R.F. Cox et al., pp. 355–362.

J. Pharm. Pharmacol., 1990, 42: 468–472, "Evaluation of In–vitro Percutaneous Absorption across Human Skin and in Animal Models", J. Pribosky et al..

Arch Neurol., vol. 49, May 1992, "Intranasal Apomorphine in Parkinsonian On–Off Fluctuations", T. Van Laar et al., pp. 482–484.

Journal of Medicinal Chemistry, 1975, vol. 18, No. 10, "Emetic Activity of N–substituted Norapomorphines", E. R. Atkinson et al., pp. 1000–1003.

Journal of Medicinal Chemistry, 1975, vol. 18, No. 10, "Emetic Activity of N–Substituted Norapomorphines", E.R. Atkinson wt al., pp. 1000–1003.*

* cited by examiner

TRANSDERMAL PATCH AND TOPICAL COMPOSITIONS COMPRISING PROPYLNORAPOMORPHINE This application is a 371 of PCT/IE99/00066 filed Jul. 15, 1999.

TECHNICAL FIELD

The present invention refers to the use of substances such as R(−)-propylnorapomorphine hydrochloride thereinafter abbreviated to R(−)-NPA-HCl, or Compound (1)] and S(+)-propylnorapomorphine hydrochloride [S(+)-NPA-HCl, or Compound (2)] and the derivatives thereof, for the treatment of Parkinson's disease, hemicrania, sexual impotence, and psychotic disorders.

More particularly, the invention also concerns a "device" (transdermal patch) for the slow release of said substances through the skin.

PRIOR ART

Apomorphine (11B–13B) has been successfully used as a drug and, especially in the veterinary field, as an emetic. It has recently been found that apomorphine (abbreviated to APO), at suitable dosages, can have beneficial effects on patients with Parkinson's disease, while at lower dosages it is useful in the treatment of hemicrania, sexual impotence and psychotic disorders (4B, 58, 6B, 7B).

In the abovementioned therapeutic indications APO is a powerful dopaminergic agonist drug, administered by the intravenous (i.v.), subcutaneous (s.c.), intramuscular (i.m.), rectal, sublingual or intranasal route. The substance is characterized by a rapid absorption, correlated with a rapid attack (latent period about 15') and an equally rapid elimination (half-life about 33') (8B).

The molecule of apomorphine is unstable on exposure to air and to light, oxidizing rapidly. When exposed to air, in fact, preparations based on apomorphine change colour, turning green, thus giving rise to a product which can no longer be used clinically.

For this reason, in order to guarantee the patient the necessary pharmacological cover, with therapeutically effective blood levels that are sufficient and constant over 24 hours, a large number of daily administrations are needed, with limited doses, of the order of 1–5 mg/hour of active principle. Exceeding such a dose by even the slightest amount causes serious side effects, such as vomiting, depression of the central nervous system (CNS) and, in some cases, even death of the patient.

Recently the administration of apomorphine by continuous subcutaneous infusion, by means of small insulin pumps which should guarantee pharmacological cover with the hourly infusion of low doses, without causing side effects, has been proposed and carried out in medical practice. But even this alternative mode of administration is not without disadvantages: already with dosages of 2–5 mg/hour, there is a tendency that subcutaneous granulomas form around the infusion site, which require the suspension of the treatment. This is due to the fact that the drug is practically concentrated at one point: around the point of the needle.

DESCRIPTION OF THE INVENTION

It is an object of the present invention to use a pharmaceutical composition based on R(−)-NPA-HCl (Compound (1)) or S(+)-NPA-HCl (Compound 2) and/or the derivatives thereof, which can be administered to the patient in therapeutically effective doses of active principle, in a continuous manner, without causing the occurrence of serious side effects, such as vomiting and depression of the central nervous system (CNS), due to a high dosage of active principle, or else granulomas around the infusion site (when the dosage is lower), as found with the use of APO.

The activity of Compounds (1) and (2) is 10 times greater than that of APO, and in addition their toxicity is lower in addition, the half-life is greater than that of APO. For this reason, when said compounds are given at suitable doses over 24 hours, effects which are rather more beneficial than those of APO are obtained.

Another object of the present invention is to produce a transdermal patch for the slow release of Compounds (1) and (2), and/or the derivatives thereof, hereinafter also called PATCH-TDSS (TDDS=Transdermal Drug Delivery System). The transdermal patch of the invention will guarantee a therapeutically effective level of Compounds (1) or (2) and/or the derivatives thereof (active principle) over 24 hours, without presenting the disadvantages of the traditional techniques.

This is because, as the patch is of relatively large dimensions (40 $cm^2$ for example), the active principle can permeate the epidermis through all the 40 $cm^2$ without any possibility of producing accumulation sites.

Moreover, the greater therapeutic activity allows the dosage to be reduced about 10 times. The greater solubility in water allows the release and index of permeation in vivo to be suitably modified by the addition of suitable permeation activators.

BRIEF DESCRIPTION OF THE DRAWINGS

The present invention will be described in greater detail with reference to some of the preferred embodiments thereof shown in the appended drawings, in which.

PREFERRED EMBODIMENTS

Figure 1:
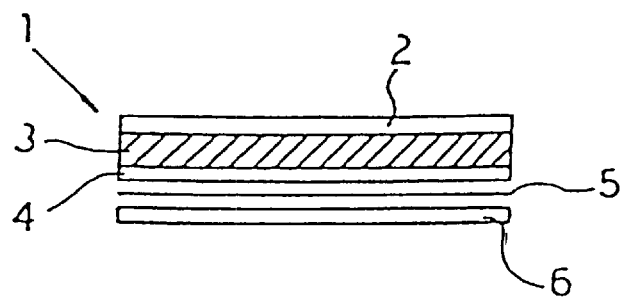
FIG. 1 is a first type of transdermal patch, according to the invention, with a permeable membrane.

FIG. 1 shows a first type of transdermal patch 1 which includes an impermeable support film 2 on which a matrix 3 is arranged. The active substance, (1), (2), and/or the derivatives thereof, is dissolved and/or dispersed in the matrix 3 which serves as a reservoir. The matrix 3, on the opposite side to the impermeable support 2, is covered by a membrane 4 permeable to the active substance, which regulates the cross-flow. This membrane may not be necessary if the degree of permeation of the active substance in the skin does not exceed the values which might cause side effects (see FIGS. 2 and 3 where this membrane is not provided).

The degree of diffusion of the active substance will also depend on the permeation activators, solubilizers, etc. On the free side of the permeable membrane 4 there is a layer of a contact glue 5 (adhesive layer), protected by a release strip 6. During the use of the transdermal patch the release strip 6 is pulled off and the patch is positioned on the desired part of the patient's body, exerting slight pressure.

After a "start" phase the flow reaches a constant "saturation" value.

The release curves of the active substances (see FIGS. 4, 5) and the plasma concentration based on a computerized model will be discussed below, with reference to the transdermal patch of Type III.

In the case of the patch 1' of Type II (FIG. 2), a matrix or "reservoir" 3, in which the active substance is dissolved and/or dispersed, is applied on the impermeable support film 2'. In the present case the membrane permeable to the active substance, which is used to modify the cross-flow, is missing. The matrix 3' therefore comes into direct contact with the epidermis. The glue 5' is located around the edge of the patch, like an adhesive ring. Everything is protected on the free side by a single release strip 6', which is removable, as for Type I.

The use of the "device" is as follows: the release strip 6' is pulled off and the device is positioned on the desired part of the patient's body, exerting slight pressure.

This solution (Type II) can be adopted in particular if the active principle interacts in an unwanted manner with the adhesive, as a result of which it is not possible to mix the adhesive 5' and the active principles in the matrix 3'.

Patch Type III is the one relating to the "drug in an adhesive matrix".

In this "device" the pharmacological dose is placed directly, dissolved or dispersed, into the glue, which thus also becomes a "reservoir" matrix 3" and which is arranged in a layer on a permeable support film 2". The adhesive matrix 3" is protected on one side by the support 2" (backing) and on the other by the release strip 6". The use of the device is as follows: the release strip 6" is pulled off and the device is positioned on the desired part of the patient's body, exerting slight pressure.

Depending on the particular application, the first, second or third type of patch will be used. It is obvious, however, that a person skilled in the art will be able to modify the shape and/or structure of the patch as he wishes, achieving the best result based on the therapy chosen and the site of application; or on other factors.

Figure 2:
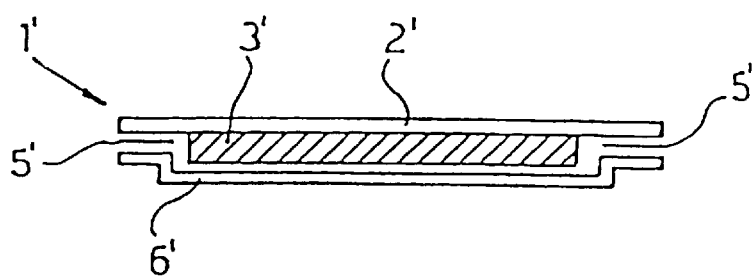
FIG. 2 is a second type of transdermal patch, according to the invention, without a permeable membrane.
Figure 3:
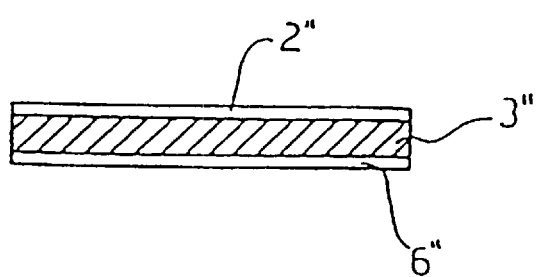
FIG. 3 is a third type of transdermal patch, according to the invention, with an adhesive matrix.

The three configurations shown in FIGS. 1, 2 and 3, therefore, are examples and not limiting.

The differences in the structure and shape of the patch (rectangular or anatomical) may be due:
- to the interactions which may exist between the active principle, the glue (different types of adhesive can be used simultaneously), the support material, and other materials such as excipients, stabilizers, etc.;
- to better stability on the chosen site of application;
- to the dosage (the area of the patch must also increase for a higher dosage).

For purposes of illustration, the method of manufacture of the patch of Type III will be discussed in the following description, and in addition the components of the pharmaceutical composition which constitutes the matrix will be indicated.

Then, three particular non-limiting examples of the pharmaceutical composition used to form the matrix of a Type III patch will be illustrated (FIG. 3). The Type III patch, containing a matrix made up of these three types of formulations, will then be "tested" on guinea-pig skin, to analyse the permeation of the active principle, both with regard to the accumulation of active principle over 48 hours (FIG. 4) and with regard to the flow (also over 48 hours, FIG. 5).

Method of Manufacture of the Transdermal Patch of Type III

1. The active principle (1) or (2) or a derivative thereof is incorporated simultaneously with the other components (stabilizer, permeation activators, etc.) in the hot adhesive solution and homogenized by stirring, until the liquid adhesive matrix or "reservoir" is obtained;
2. the liquid matrix is cooled, and acquires a "stringy" consistency;
3. the process for layering of the adhesive matrix on the support is carried out using a layering machine which is continuously connected with a drying machine, in the following phases:
    the blade of a knife is mounted across the entire width of the conveyor belt of the layering machine on which the release strip is securely positioned;
    the "stringy" adhesive matrix is poured in front of the blade, which, as the conveyor belt advances, distributes a uniform layer (layering) of adhesive matrix on the release strip;
    the thickness of the layer is mainly determined by the distance between the edge of the knife blade and the release strip running beneath it;
    the release strip, carrying the adhesive matrix, rotates inside the drying machine, in which the adhesive matrix is solidified by evaporation of the solvent, which is achieved by gradually increasing the temperature and the "ventilation", as shown in the following Table I.

TABLE I

| Drying phase | Time (in minutes) | T ° C. | Vent. (rpm) |
|---|---|---|---|
| 1 | 15 | 40 | 700 |
| 2 | 20 | 55 | 1000 |
| 3 | 25 | 70 | 1200 |

The process described allows elimination of the solvent, preventing it from being occluded by the rapid formation of a surface crust.

When the adhesive matrix has dried, the support film (backing) is applied. This phase, called "lamination", ends the process.

The process is described in the literature (9B, 10B, 11B) and gives rise to a PATCH-TDDS in which the adhesive matrix remains protected both by the "backing" and by the removable release strip.

It is very important to use an adhesive which is inert and permeable to (1) or (2) and the derivatives thereof, and the adhesive properties of which (cohesion, adhesion and interlacing) are not adversely affected by the active principle itself and/or by excipients or any other material added.

Composition of the Type III PATCH-TDDS

Adhesive Matrix: Formulation
   active principle: (1) or (2) or derivatives thereof;
   antioxidant: sodium metabisulphice, EDTA disodium salt;
   solubilizing agent: a glycol;
   permeation activator: fatty acids;
   acrylic resin to improve the cohesive strength: cationic copolymers based on dimethylaminoethylmethacrylate and methacrylic esters;

cellulose derivatives to improve the cohesive strength: ethylcellulose;

surfactant: SDS (sodium dodecylsulphate);

pressure contact adhesive: mixture of two adhesives, A and B, in which A is a non-self-bonding acrylic contact adhesive of medium molecular weight with a high interlacing index, with a skin irritation index of 0.20, classified as "minimally irritating", using 100% ethylacetate as solvent; and B is a self-bonding acrylic adhesive with a high molecular weight, with moderate interlacing, with a skin irritation index of 0, classified as "non-irritating", using a mixture of ethylacetate, isopropanol, hexane and toluene as solvent.

Release Strip

The release strip is a polyester film laminated with silicone on one side (that opposite of the adhesive matrix). The thickness is approximately 125 µm.

"Backing"

The "backing" is a laminated polyester film which is clear and occlusive with a themoweldable layer. The total thickness is approximately 51 µm.

Quantity of Active Principle

The quantity of (1) or (2) or derivatives thereof, expressed as (1) or (2), is 5% by weight of the adhesive matrix and corresponds to 5 mg/cm$^2$ in the PATCH-TDDS. The major part of the drug is dispersed in the matrix. A minor part is dissolved in the matrix. The drug dispersed in the matrix acts as a "reservoir", while the drug available for release and permeation is the dissolved drug.

Three examples of the efficacy in application of the Type III transdermal patch based on (1) or (2) and/or derivatives thereof are now given.

Three batches of patches of differentiated formulation containing (1) or (2) and/or derivatives thereof were prepared for this purpose.

Using the in vitro cell permeation technique recommended by the FDA in the USA (1B, 2B, 3B), the following results were obtained, for example, with three different formulations given below, where Compound (1) was used as the active principle, i.e. the pharmacologically most active molecule:

EXAMPLE A

| 1) Compound (1) | 2.00% |
|---|---|
| 2) Sodium metabisulphite | 0.20% |
| 3) Solubilizing agent | 4.00% |
| 4) Acrylic resin | 29.00% |
| 5) Fatty acid 1 | 3.20% |
| 6) Fatty acid 2 | 1.60% |
| 7) Pressure-sensitive adhesive | 60.0% |

EXAMPLE B

Batch R(−)-NPA-HCl/B, with addition of permeation inducers, active principle dispersed in the matrix (reservoir) 4.5%. active principle dissolved in the matrix 0.5%.

| 1) Compound (1) | 4.99% |
|---|---|
| 2) Sodium metabisulphite | 0.50% |
| 3) EDTA | 0.025% |
| 4) Solubilizing agent | 9.96% |
| 5) Fatty acid 1 | 7.96% |
| 6) Fatty acid 2 | 3.97% |
| 7) Acrylic resin | 1.99% |
| 8) Cellulose derivative | 0.25% |
| 9) Surfactant | 19.90% |
| 10) Pressure-sensitive adhesive | 50.455% |

EXAMPLE C

Batch R(−)-NPA-HCl/C, with addition of permeation inducers, active principle 0.5% in the matrix (all of the drug is dissolved):

| 1) Compound (1) | 0.50% |
|---|---|
| 2) Sodium metabisulphite | 0.50% |
| 3) EDTA | 0.025% |
| 4) Solubilizing agent | 9.96% |
| 5) Fatty acid 1 | 7.96% |
| 6) Fatty acid 2 | 3.97% |
| 7) Acrylic resin | 1.99% |
| 8) Cellulose derivative | 0.25% |
| 9) Surfactant | 19.90% |
| 10) Pressure-sensitive adhesive | 50.945% |

Experimental Results

Figure 4:
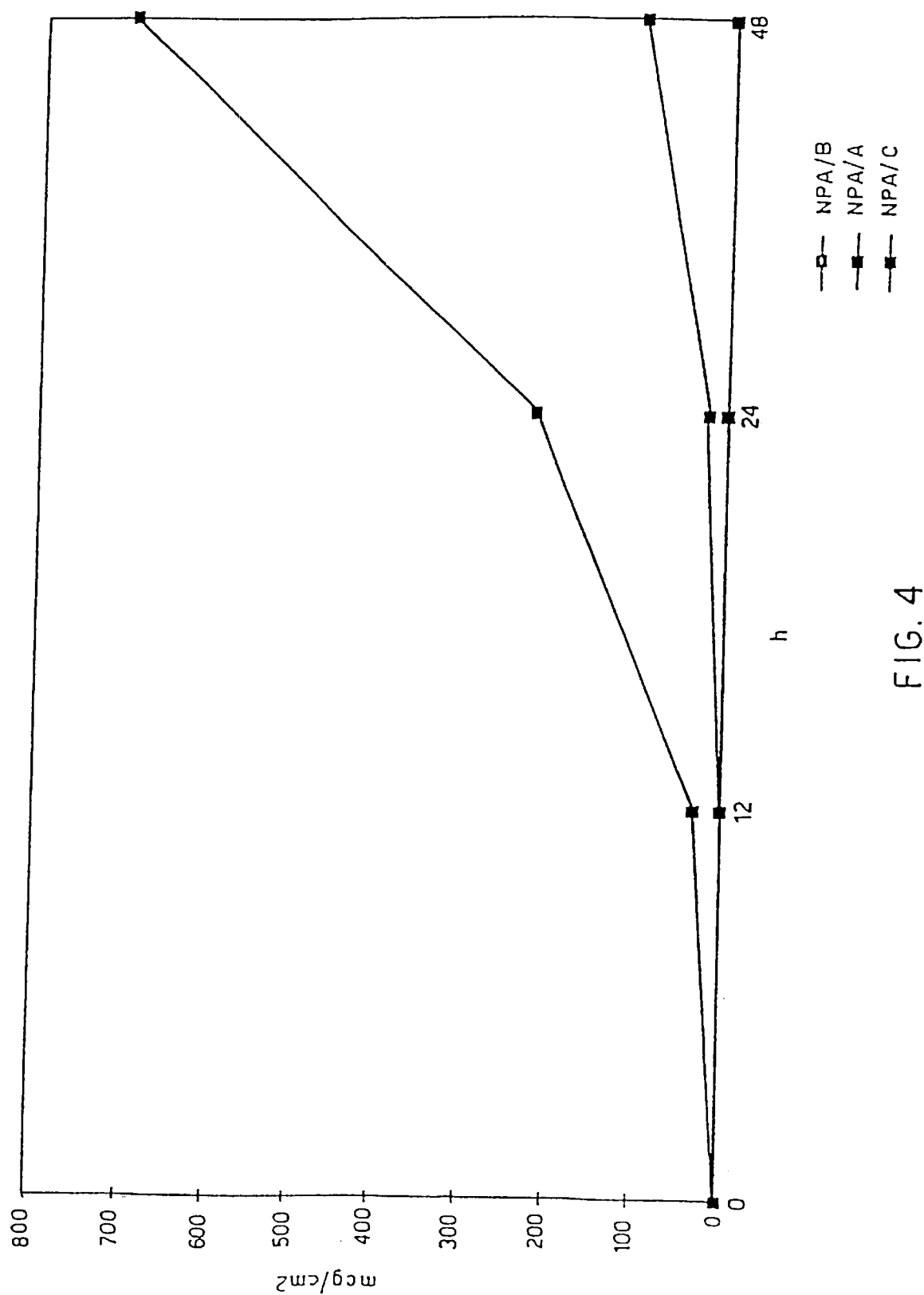
FIG. 4 is a diagram of the permeation of Compound (1) in vitro on guinea-pig skin (accumulation)
Figure 5:
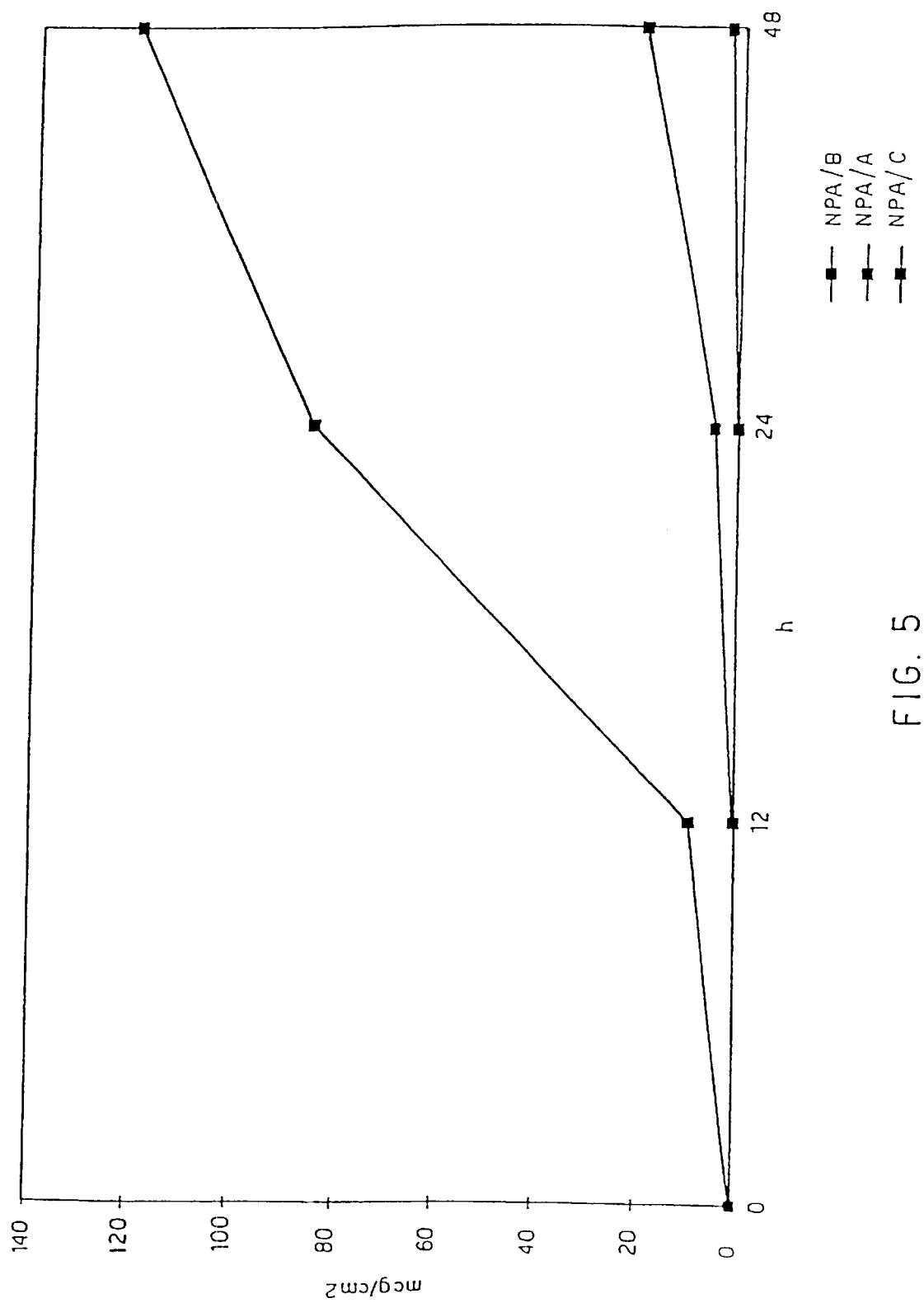
FIG. 5 is a diagram of the permeation of Compound (1) in vitro on guinea-pig skin (flow per unit of time)

The in vitro permeation study with guinea-pig skin, carried out in accordance with the stated procedures, showed a permeation rate equal to the values given in FIG. 4 (total quantity) and in FIG. 5 (flow), for the three examples A, B and C, at the different times.

It can be observed that in the case of Example C the values are almost zero, i.e. all the black squares are virtually located on the axis of abscissae (time, in hours).

This demonstrates that a quantity of 0.5% of active principle dissolved in the matrix, in the absence of a certain quantity of dispersed active principle, does not produce an appreciable permeation of the active principle through the skin such as to permit the use envisaged.

It will therefore be necessary to disperse a certain quantity of active principle in the matrix, in such a way as to produce a concentration gradient which facilitates the diffusion of the active principle, as well as constituting a "reservoir", in order to obtain a slow release.

Figure 6:
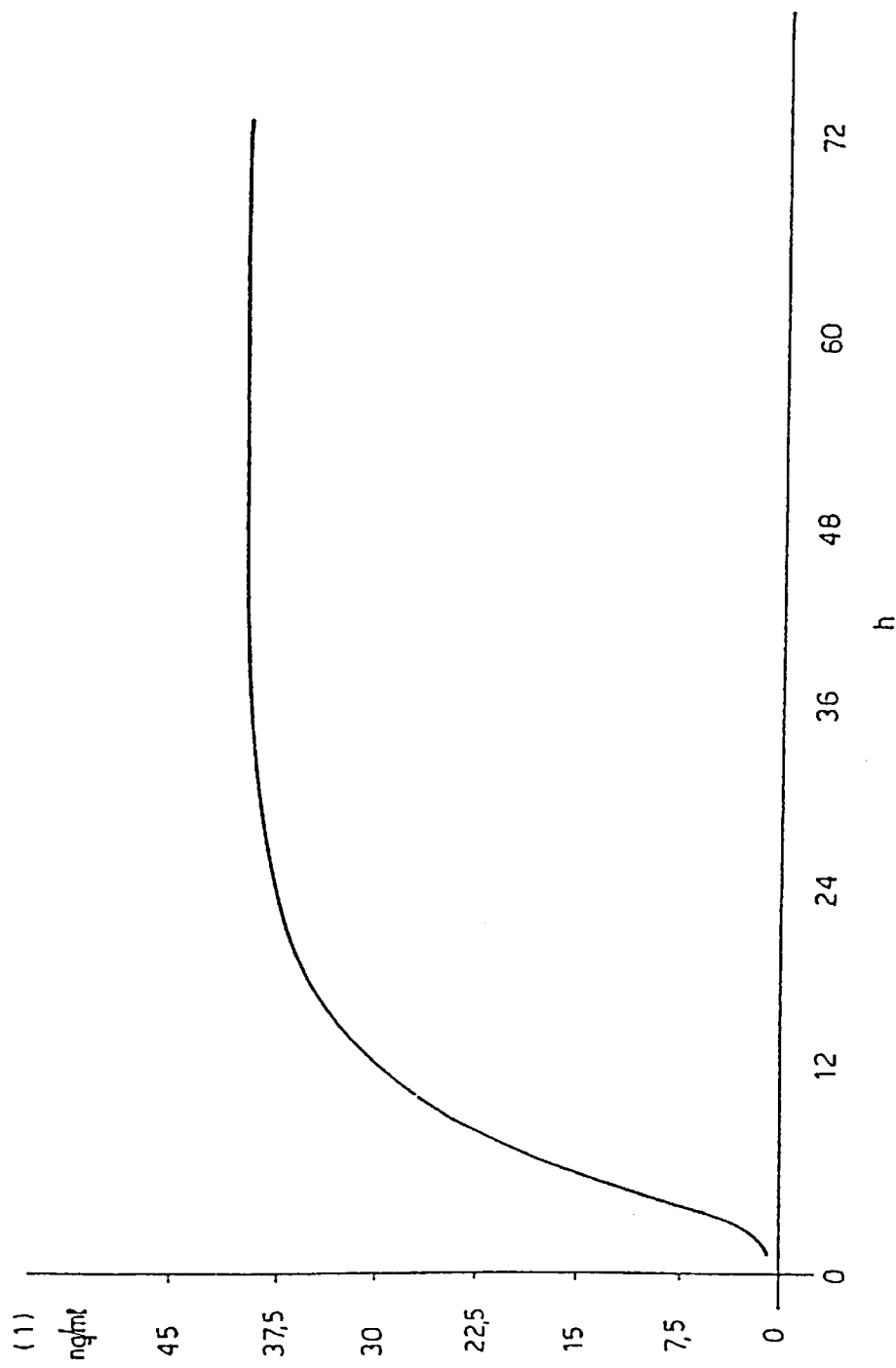
FIG. 6 is a diagram which shows the approximate curve representing human plasma levels at the times indicated (in hours (h)) relative to the active principle (1).

On processing the in vitro permeation data reported above with one of the most appropriate pharmacokinetic models for the transdermal administration of the drugs (10B, 11B), and considering a patch of 40 cm$^2$ (5×8 cm) with the following constants:

| molecular weight of propylnorapomorphine hydrochloride | 331.8 |
|---|---|
| water/alcohol distribution coefficient | 0.0005 |
| half-life | 45 |
| distribution volume | 132 | the approximate curve shown in FIG. 6 is obtained, representing the human plasma levels at the times indicated, in the case of application of a single Batch NPA/B patch (ordinate: unit ng/ml; abscissa: time in hours).

From FIGS. 4 to 6, it is possible to conclude that the skin permeability of Compound (1) is in itself sufficient and modifiable upwards and downwards using different permeation activators such as fatty acids or alcohols.

All the in vitro permeation studies were carried out using models which use guinea-pig skin, which we know has a permeability comparable to human skin and gives more reproducible results than the latter.

The chemical stability of Compound (1) in the formulation of the patch is achieved by the addition of an antioxidant (sodium metabisulphite) and is demonstrated with an accelerated stability test of 15 days at 40° C. and 75% RH (relative humidity).

The surfactant (SDS) is added with the aim of solubilizing a greater quantity of Compound (1), as only the solubilized substance (1) is available to be released and permeated. The patches have also exhibited good physicochemical properties which can be optimized by persons skilled in the art with regard to adhesivity at the site of application and tolerability by the subject under treatment without modifying the permeation rate of the active principle.

As has been said previously, the most appropriate configuration of the transdermal patch varies depending on circumstances. The Type III patch, for example, can be cut from a tape of greater dimensions, to obtain a transdermal patch of the appropriate size for the site of application.

The Type II patch, on the other hand, will already have to have the final dimensions, and cannot be cut, as the matrix 3' is not adhesive and the glue is limited to the annular region 5'.

BIBLIOGRAPHY

1B. Gummer LC, Chapter 9, "The in vitro Evaluation of Transdermal Delivery". In "Transdermal Drug Delivery Developmental Issues and Research Initiatives", published by Hadgraft J e Guy RH. Marcel Dekker, Inc., New York (1989)

2B. Tojo K, chapter 6, "Design and Calibration of in vitro Permeation Apparatus". In "Transermal controlled Systemic Medications", published by Chien YW. Marcel Dekker, Inc., New York. (1987)

3B. Priborski j e Muhulbachova E, "Evaluation of In vitro Percutaneous Absorption across Human Skin and in Animal Models". j. Pharm. Pharmacol. 42;468–472 (1990)

4B. T. VAN LAAR and ENH JANSEN, "Rectal apomorphine: a new treatment modality in Parkison's disease". J. Of Neurology, Neurosurgery and Psychiatry 55;737–737 (1992)

5B. T. VAN LAAR et A.: "Intranasal Apomorphine in Parkinsonian on-off fluctuations". Arch. Neurol. Vol. 49,482–484, May (1992)

6B. W. Poewe et Al. "Continuous Subcutaneous Apomorphine Infusions for Fluctuating Parkison's Desease". "Advances in Neurology", vol. 60, 656–659. Reven Press Ltd New York (1993)

7B. E. Nicolle et Al. "Pharmacokinetics of apomorphine in parkinsonian patients". "Fundam. Clin. Pharmacol." 7:245–252 (1993)

8B. E. Sam. et Al. "Stability of apomorphine in plasma and its determination by high-performance liquid chromatography with electrochemical detections". J. of Chromatography B. 658:311–317 (1994)

9B. Satas D. Chapter 34, "Coating equipment". In Handbook of Pressure Sensitive Adhesive Technology. Donatas Satas, eds. New York. van Nostrand Reinhold 809–830 (1989)

10B. Grand OW and Satas D, chapter 4, "Other Knife and Roll Coaters" In "Web Processing and Coverting Technology and Equipment". Donatas Satas eds. New York, Van Nostrand Reinhold 60–80 (1984).

11B. Elias JJ, chapter 1, "The Microscopic Structure of the epidermis and its Derivatives". In Percutaneous Absorption", published by Bronaugh RL and Maibach Hl. Marcel Dekker, Inc. New York (1989).

12B. Nora S. Kula, Ross J. Baldessarini et Al. "Effects of Isomers of Apomorphines on dopamine receptors in striatal and limbic tissue of rat brain". "Life Sciences", vol. 37, pp. 1051–1057.

13B. John L. Neumeyer et Al. "Aporpines. 48.Emantioselectivity of (R)-(-)- and (S)-(+)-N-n-Propylnorapomorphine on Dopamine Receptors". J. Med. Chem. 1983, 26, 516–521.

14B. Richard F. Cox and Al. "Effects of N-n-Propylnorapomorphine Enantiomers on single Unit Activity of Substantia Nigra Pars Compacta and Ventral Tegmental Area Dopamine Neurons". "The Journal of Pharmacology and Experimental Therapeutics"; 1988, 7, pages 355–362.

What is claimed is:

1. A transdermal patch comprising: at least one support film; an intermediate matrix comprising a pharmaceutical composition; and a protective release strip, wherein the pharmaceutical composition comprises an active principle selected from one or more components of the group consisting of R(−)-propylnorapomorphine hydrochloride, S(+)-propylnorapomorphine hydrochloride, derivatives of R(−)-propylnorapomorphine hydrochloride and derivatives of S(+)-propylnorapomorphine hydrochloride, in pharmaceutically acceptable and effective doses, and further comprising components selected from the group consisting of stabilizers, solubilizers and permeation activators to facilitate the passage of the active principle through skin.

2. A transdermal patch according to claim 1, wherein said derivatives of R(−)-propylnorapomorphine hydrochloride and derivatives of S(+)-propylnorapomorphine hydrochloride are salts or organic derivatives.

3. A transdermal patch according to claim 1, wherein said stabilizers are antioxidant substances.

4. A transdermal patch according to claim 1, wherein said solubilizer is a glycol.

5. A transdermal patch according to claim 1, wherein said permeation activators are fatty acids or alcohols.

6. A transdermal patch according to claim 3, said antioxidant substance comprises sodium metabisulphite and EDTA.

7. A transdermal patch according to claim 1, wherein the pharmaceutical composition additionally comprises a surfactant.

8. A transdermal patch according to claim 1, wherein the pharmaceutical composition additionally comprises an acrylic resin to improve the cohesive strength, cellulose derivatives to improve the cohesive strength, and a mixture of pressure contact adhesives.

9. A transdermnal patch according to claim 1, wherein said matrix comprises a lower side layer comprising a permeable membrane that does not include adhesives.

10. A transdermal patch according to claim 9, wherein said permeable membrane modifies the release of the active principle and is an adhesive layer for fixing on the skin.

11. A transdermal patch according to claim 9, wherein said permeable membrane is not adhesive and has an adhesive layer underneath for fixing on the skin.

12. A transdermal patch according to claim 1, wherein an adhesive layer is applied on sides of the matrix not containing adhesives.

13. A transdermal patch according to claim 1, comprising an adhesive matrix containing an acrylic resin, cellulose derivatives to improve the cohesive strength, and a mixture of pressure contact adhesives.

14. A method of treatment of a disorder selected from the group consisting of Parkison's disease, hemicrania, sexual impotence and psychotic disorders, comprising the step of administering the transdermal patch of claim 1 to obtain slow release of the active component through the skin.

15. A transdermal patch according to claim 7, wherein said surfactant is sodium dodecyl sulfate.

* * * * *